(12) United States Patent
Haislip

(10) Patent No.: US 7,832,032 B2
(45) Date of Patent: Nov. 16, 2010

(54) MULTIPURPOSE SLEEPING BAG

(76) Inventor: Richard E. Haislip, 2223 Commerce Pkwy., Virginia Beach, VA (US) 23454-4301

( * ) Notice: Subject to any disclaimer, the term of this patent is extended or adjusted under 35 U.S.C. 154(b) by 0 days.

(21) Appl. No.: 12/418,143

(22) Filed: Apr. 3, 2009

(65) Prior Publication Data
US 2010/0256716 A1 Oct. 7, 2010

(51) Int. Cl.
*A47G 9/08* (2006.01)
*A41D 3/00* (2006.01)

(52) U.S. Cl. ............... 5/413 R; 5/485; 5/482; 2/69.5; 2/69

(58) Field of Classification Search ......... 5/413 R, 5/413 AM, 494, 485, 482; 2/69, 69.5; 219/212
See application file for complete search history.

(56) References Cited

U.S. PATENT DOCUMENTS

| 608,351 | A | * | 8/1898 | Terramorse | 2/89 |
|---|---|---|---|---|---|
| 1,102,408 | A | * | 7/1914 | Hubner | 2/93 |
| 2,644,948 | A | * | 7/1953 | Gutmann | 2/69.5 |
| 3,381,306 | A | * | 5/1968 | Innes | 2/69 |
| 3,427,431 | A | * | 2/1969 | Costanzo | 219/212 |
| 3,443,066 | A | * | 5/1969 | Weibel | 219/527 |
| 3,986,505 | A | * | 10/1976 | Power | 128/846 |
| 4,167,604 | A | | 9/1979 | Aldrich | |
| 4,484,362 | A | * | 11/1984 | Asher | 2/69 |
| 4,579,753 | A | * | 4/1986 | Gjendemsjo | 428/17 |
| 4,703,521 | A | | 11/1987 | Asher et al. | |
| 4,759,082 | A | | 7/1988 | Mulligan | |
| 4,895,171 | A | * | 1/1990 | Onik | 5/413 R |
| 5,257,427 | A | * | 11/1993 | Hinshaw | 5/613 |
| 5,490,294 | A | | 2/1996 | Kramer | |
| 6,338,173 | B1 | | 1/2002 | Ramsey | |
| 6,393,637 | B1 | * | 5/2002 | Hoffman | 5/413 R |
| 7,647,656 | B2 | * | 1/2010 | Smith | 5/413 R |
| 2007/0061965 | A1 | * | 3/2007 | Crawford | 5/413 R |
| 2007/0136946 | A1 | * | 6/2007 | Haislip | 5/413 R |
| 2008/0028518 | A1 | * | 2/2008 | Miotke et al. | 5/482 |
| 2008/0078027 | A1 | * | 4/2008 | Smith | 5/13 R |

OTHER PUBLICATIONS

Ecotat, "All in One Freedom Shelter" promotional material.

* cited by examiner

*Primary Examiner*—Robert G Santos
(74) *Attorney, Agent, or Firm*—Brundidge & Stanger, P.C.

(57) ABSTRACT

A multipurpose sleeping bag has an opening in the center that can be drawn around one's neck in an over garment mode, or closed in a sleeping bag mode. A draw cord is employed to compress a foot portion and, optionally, a foot draft tube, into a knot-like configuration for the sleeping bag mode. For operations other than the sleeping bag mode, the foot portion is left open to form a skirt-like configuration. Another embodiment configures a multipurpose hypothermia sleeping bag, which includes flap panels positioned on the top side thereof to provide an opening for IV or catheter administration to a hypothermia patient. Each flap panel can also accept a heating device. Chest and back pockets, respectively above and below the head opening, accept heating devices to provide warmth while using the sleeping bag in an over garment mode of operation.

17 Claims, 17 Drawing Sheets

MULTIPURPOSE SLEEPING BAG

BACKGROUND OF THE INVENTION

1. Field of the Invention

This invention relates generally to a multipurpose sleeping bag, and more particularly to a sleeping bag that can be converted into an anorak (short coat), cagoule (long coat), poncho, quilt, or vehicle blanket, or be joined to another multipurpose sleeping bag so as to provide a higher degree of warmth.

This invention also relates to a new and useful structural refinement in such sleeping bags for the military and civilians, such as sportsmen, hunters, campers, etc., which can also be worn as an over garment. In particular, this invention, even when converted into an anorak, cagoule, poncho, quilt or vehicle blanket, can be refined structurally to accept state-of-the-art, silicone rubber heating units in the torso, chest and back areas of the sleeping bag.

2. Description of the Related Art

Present-day sleeping bags currently available on the market are not designed to be used as an anorak, cagoule, poncho, quilt, or vehicle blanket, or to be joined to another sleeping bag. Currently, people who want the above combination of items must carry them as separate items. The disadvantages of carrying separate items of equipment, such as those stated above, are additional cost and increased weight and bulk.

Further, while sleeping bags for the military and civilians are well known in the art, such bags are inappropriate to provide panels for accepting state-of-the art microprocessor heating units that provide heat to the user, or for treatment of hypothermia casualties.

Unlike other warm-blooded animals that have a layer of hair to keep them warm, humans need an extra layer of clothing or heating devices to keep them warm when the weather is cold. Without that extra layer of clothing, more heat escapes from the body than the body can produce. If too much heat escapes, the result is hypothermia, or abnormally low body temperature. Hypothermia is also often the result of a trauma condition.

Hypothermia can make one sleepy, confused, clumsy and because it happens gradually, it can affect one's thinking. Therefore, a hypothermia victim may not realize that he needs help and that makes it especially dangerous. A body temperature below 95° F. (35° C.) is a medical emergency and can lead to death if not treated promptly.

In addition, a caregiver in the outdoors often infuses cold IV fluid into a patient during evacuation. Because this fluid is at ambient temperature, which may be much lower than the proper core body temperature, the patient may suffer a decrease in temperature, again leading to hypothermia.

SUMMARY OF THE INVENTION

Addressing a recognized need, this invention reduces the number of items, as well as the weight and bulk, which must be carried by campers and mountaineers.

It is another object of the present invention to provide a multipurpose sleeping bag which can easily be converted from one use to another. Specifically, the invention can be configured as a single sleeping bag or worn as a long coat, short coat, poncho, quilt, or blanket, and to provide its own heating capability to provide warmth to the individual in any of these configurations. In addition, such a multipurpose sleeping bag is capable of allowing the user to adjust his warmth inside the bag to any exposure he might encounter whether in a static or mobile mode of operation. Furthermore, such a multipurpose sleeping bag is capable of providing a means of allowing any IV fluids, being administered to a patient even in a cold environment, to be as close to the patient's body temperature as possible.

It is a further objective of the present invention to provide a convertible sleeping bag structure which can easily be converted from a sleeping bag into an over garment, such as a long coat, short coat, or poncho, while at the same time giving the wearer the means to increase his warmth, with the state-of-the-art heating units of today.

It is yet a further objective of the present invention to provide a convertible sleeping bag structure which is both easy for the user to convert as well as inexpensive in the cost of production.

The present invention provides a multipurpose sleeping bag which can be adapted to provide protection from cold weather while walking, riding, sitting, or reclining. The invention provides a single piece of equipment which is lightweight and which can quickly and easily be converted from one use to another. Specifically, the invention can be configured as a single sleeping bag, long coat, short coat, poncho, quilt, or vehicle blanket and can be readily joined with a second multipurpose sleeping bag so as to provide a higher degree of warmth.

In a specific preferred embodiment, the invention comprises a multipurpose hypothermia sleeping bag (MHSB) that is cost effective in providing heat for the treatment and prevention of hypothermia patients. Post trauma patients are highly susceptible to shock following injury and surgery. It is imperative to maintain the patient's body temperature while awaiting or during transport. This embodiment can provide heating panels for the front torso, chest and back part of the body for hypothermia patients. It can also be converted into various forms, as stated above, thereby providing a single piece of equipment which is lightweight and which can quickly and easily be converted from one use to another.

The invention includes a body portion having a top, a bottom and at least two major sides. The body portion is capable of enclosing the torso of the user and also has openings situated about the body portion to accommodate the extremities of the user. These openings include access for the legs and the head. Another opening is located on the back of the body portion to provide access for the head of the user when the person desires to use the sleeping bag as an over garment.

In the MHSB embodiment, the body portion also has two patient access panels (called "torso access panels") located on the front of the MHSB, including one on the left and one on the right side of the MHSB. These torso access panels are, for example, 36" long by 12" wide, separated from the panel with a mesh lining that is designed to receive a silicone rubber heater pad so as to provide heat for any casualty or hypothermia victim. If the patient requires catheterization or IV fluids, the catheter or IV line is routed into the bag next to the mesh and the heating pad. In this case, the IV fluid can come close to the body core temperature. Inside the body portion, on the back and sides, are additional mesh panels (e.g., 11" by 11") designed to receive a 10" by 10" (e.g.) silicone rubber heating pad. This provides heat for the chest and back part of the body when the user desires to wear the MHSB as an over garment such as a poncho, when dealing with ambulatory casualties. The MHSB also allows the caregiver to choose the location of the heating pads, for posterior or anterior warming, for example, depending on the patient's injury or medical protocol.

BRIEF DESCRIPTION OF THE DRAWINGS

The various features and advantages of the present invention will become more apparent by reading the following detailed description in conjunction with the drawings and where like reference numerals identify corresponding components, as shown in the accompanying drawings, in which:

FIG. 15(*b*) is a side view of a mesh panel attached to one of the torso and IV access panels, forming a torso and IV access panel pocket.

FIG. 15(*c*) is a perspective view of the front side showing the positioning of the torso and IV access panels with one flap panel opened for access to the torso.

DETAILED DESCRIPTION OF THE PREFERRED EMBODIMENTS

Figure 1:
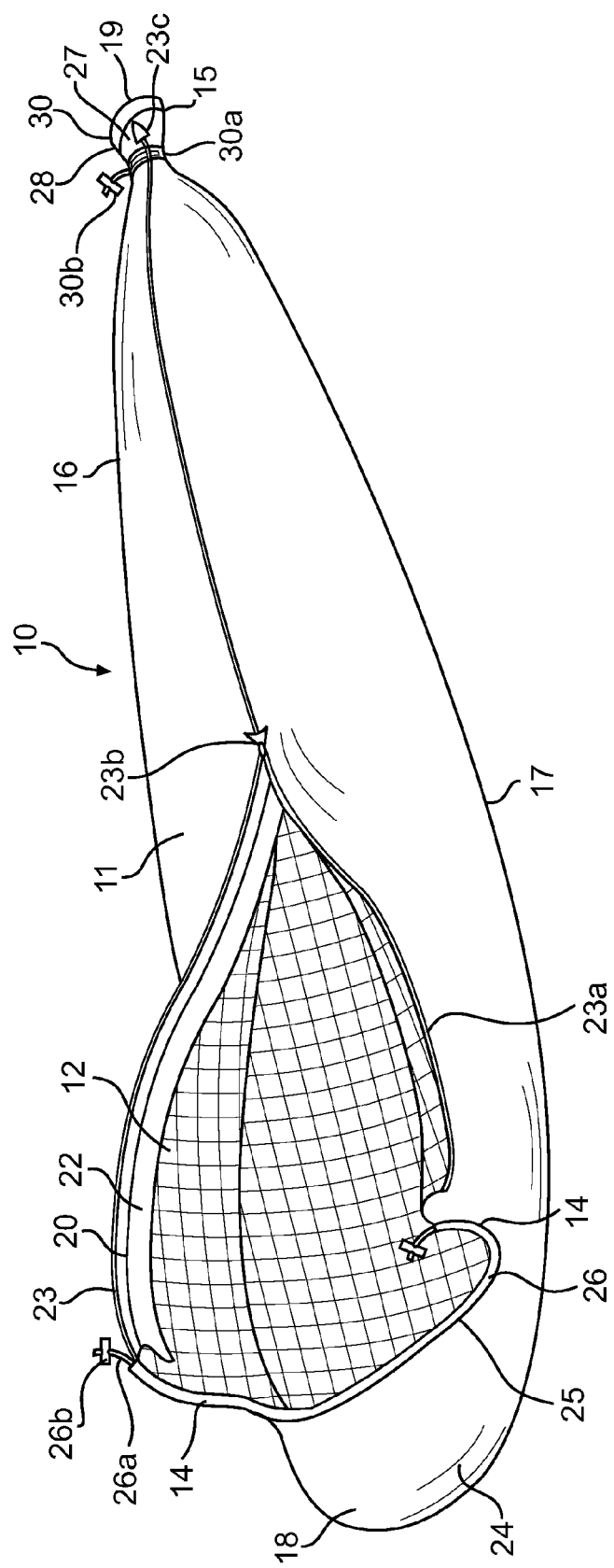
FIG. 1 is a perspective view illustrating a preferred embodiment of the invention as a sleeping bag.

Referring now to the drawings in more detail and particularly to FIGS. 1 through 6, it will be seen that the invention, as illustrated in currently preferred embodiments, is a trapezoidal-shaped multipurpose sleeping bag of unitary construction, indicated generally at 10. Preferably, the multipurpose sleeping bag comprises three flexible layers: an external shell 11, an internal lining 12, and insulation material 13, positioned between the external shell 11 and the internal lining 12 (see FIG. 5). The external shell 11 and the internal lining 12 are preferably made of 70-denier nylon, commonly known as single-ply taffeta. The 70-denier refers to the thickness of the yarn. The actual weave may be, for example, 86 yarns in one direction and 104 yarns in the other, per square yard. The thickness of the yarn should be chosen to absorb body heat and quickly warm to body temperature, because the faster this warming occurs, the slower will be the rate of conductive heat loss from the body. Furthermore, the spaces between yarns in this construction allow the moisture produced by the body to easily escape. Even in a dry climate, the body gives off moisture. Therefore, it is important to allow this moisture easy exit. Indeed, water is extremely efficient at absorbing heat, so one always wants to stay as dry as possible.

The insulation material or fiberfill 13, positioned between the external shell 11 and the internal lining 12, preferably comprises an unbounded, silicone-coated continuous-filament fiber. The silicone coating gives the fiber two very desirable properties. The first is an antistatic property, which allows the fibers to perpetually repel each other; regardless of how tightly the fibers are packed against each other (such as when the invention is compacted in a stuff sack). This property also contributes to the loft always returning after the multipurpose sleeping bag 10 is removed from the stuff sack. The second beneficial property of the silicone treatment is in making the fiber hydrophobic. Water simply does not attach itself to the fiberfill 13.

It is extremely important that the moisture leaving the body be able to pass through the spaces between the yarns of the external shell 11 and the internal lining 12, and to easily move through the insulation material 13. Also, it is imperative that the moisture not be able to condense in the insulation material 13. If this occurs when temperatures are below freezing, frost buildup can severely reduce the thickness of the insulation material 13, or the moisture may simply freeze as in any other sleeping bag, and thus add weight. More specifically, fibers that are touching each other cause conductive heat loss, and when fibers chill, the moist vapor is cooled rapidly, changing it to liquid and then ice, further endangering subjects whose bodies dehydrate much more rapidly in extreme cold climates than in hot climates. The insulation material 13, on the other hand, is quite different with respect to water. Because the fibers are antistatic and repel each other, and are not compacted from a quilting process, the moisture moves more easily through the insulation material 13. This movement of moisture is further enhanced by the silicone treatment of the fiber. Thus, the silicone acts like a lubricant, which allows the moisture to move approximately 16 times more rapidly through the insulation material 13. In extreme cold conditions, the more rapidly one's own moisture dissipates, the better.

In addition, quilting produces a fiberfill that is so densely packed that a wall is created. While this wall of synthetic fiber insulation does not absorb moisture, it inhibits the flow of moisture, which condenses in the sleeping bag.

By eliminating quilting with laminating the insulation material 13 to the internal lining 12, the insulation material is prevented from drifting around haphazardly inside the sleeping bag and creating uneven insulation, resulting in cold spots. This laminating procedure also permits less insulation material to be used, which in turn permits a lighter-weight multipurpose sleeping bag.

Even though insulation material 13 is described as a synthetic unbounded, silicone-coated continuous filament fiber, the multipurpose sleeping bag 10 can be made from any other suitable insulation filling.

The insulation material 13 also allows the body's thermostat to function more easily. The body's heating mechanism is constantly turning off and on to compensate for heat loss or heat build up. Thus, the body is continuously generating moisture, which is emitted through the pores of the skin. If the flow of this moisture is blocked or absorbed by the insulation, then that moisture becomes the enemy. Significantly, one can live a lifetime in a climate with an ambient air temperature of 45° F., but only an hour or so in water that is 45° F. Moreover, if the air temperature is below the freezing point, the moisture trapped in the insulation may freeze. This is especially a problem in extreme cold conditions such as are found in the arctic. Evaluation of many sleeping bags shows an approximate weight gain of five or ten pounds of ice per week. Consequently, body heat is conducted away by the ice forming in the prior art bag. The insulation material 13 of the present invention is a less-restrictive insulation with respect to the flow of moist air.

All three layers 11, 12, and 13 extend the length and width of the multipurpose sleeping bag and have their entire edge portions joined to each other along their lengths by, e.g., zippers and/or stitching, or other suitable means, as discussed more fully below.

FIG. 1 shows that the multipurpose sleeping bag 10 includes four sides (right or "east" side 16, left or "west" side 17, top or "north" side 18, and bottom or "south" side 19) in the sleeping bag mode of operation. As FIG. 1 shows, sides 16 and 17 are provided with separable fastener halves 23 and 23a (illustratively forming a zipper, in a preferred embodiment). These fasteners preferably form a two-way zipper, with a double slider 23b, 23c opening the zipper from the top "north" side 18 and bottom "south" side 19, respectively. By reference to FIGS. 1 and 2, it will be seen that fastener halves 23 and 23a extend substantially the length of the multipurpose sleeping bag 10. Hereinafter, fastener halves 23 and 23a will be termed "zippers" or "zipper halves", or collectively "zipper 23", but the person of ordinary skill will understand that these terms are representative only and not limitative of the invention.

External shell 11 preferably extends over the top and around the bag, and is sewn together as at 15 along the bottom center portions of the multipurpose sleeping bag 10. Further, layers 11, 12, and 13 are joined to each other along the length of zipper halves 23, 23a and by assembly stitching 14 around the radius of the head portion at top or "north" side 18 and the foot portion at bottom or "south" side 19, and at the head opening 40 of the multipurpose sleeping bag 10. Layers 11, 12, and 13 are also preferably stitched to right or "east" side 16 along with a 1½-inch strip of black webbing, for example, to act as a zipper guard 20. The zipper guard 20 keeps zipper 23 from getting caught in the internal layer 12. Zipper guard 20 is inserted on the inside of zipper 23 and layers 11, 12, and 13, and held by stitching 21.

Directly behind zipper 23 (for example, 1½ inches to the left) is placed a zipper draft tube 22. The zipper draft tube 22 keeps the heat within sleeping bag 10 from escaping through the zipper 23, and is stitched to layers 12 and 13. Layers 11, 12, and 13 are further stitched to "west" side 17 along with zipper half 23a.

Again with reference to FIG. 1 and FIG. 2, when the sleeping bag portions 11, 12, and 13 are sewn together, the sleeping bag hood portion 24 is sewn and forms the hood edge 25. A hood draw cord sleeve 26 is sewn to hood edge 25, through which runs a hood cord 26a to selectively draw the hood around the head of the wearer when used in the sleeping bag mode. A slide 26b is provided to engage each end portion of hood cord 26a to retain the hood opening in the desired position.

Figure 7:
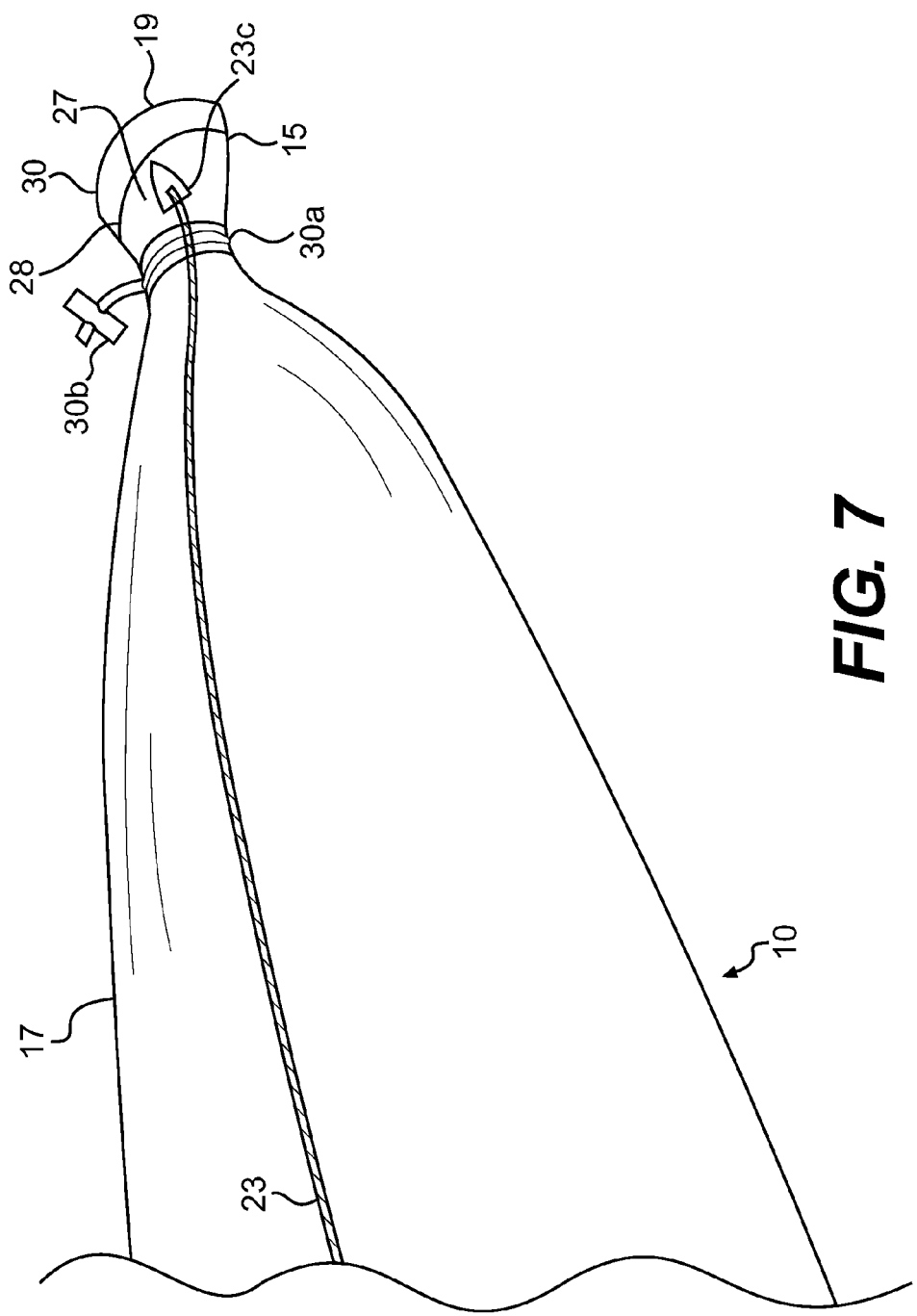
FIG. 7 is an enlarged perspective view taken of the foot end as shown in FIG. 1.

Another important feature of the invention is the provision of an open foot portion, shown in FIG. 1 and in an enlarged view in FIG. 7. Again, when layers 11, 12, and 13 are sewn together, the sleeping bag foot portion 27 forms the bottom foot edge 28. A foot draw cord sleeve 30 is sewn to edge 28. The foot draw cord sleeve 30 has a foot draw cord 30a and slide 30b, similar to hood cord 26a and slide 26b discussed above. When the multipurpose sleeping bag 10 is zipped into the sleeping bag mode of operation, the foot draw cord 30a provides the capability of drawing the bottom portions of layers 11, 12, and 13 together and wrapping the foot draw cord 30a around layers 11, 12, 13 and edge 28, thereby closing off the open foot portion. This arrangement increases the amount of insulation around the feet of the user and keeps the heat within the bottom "south" side 19 from escaping using the slide 30b to retain the bottom opening to the correct tightness as the user demands in the sleeping bag mode of operation.

Figure 6:
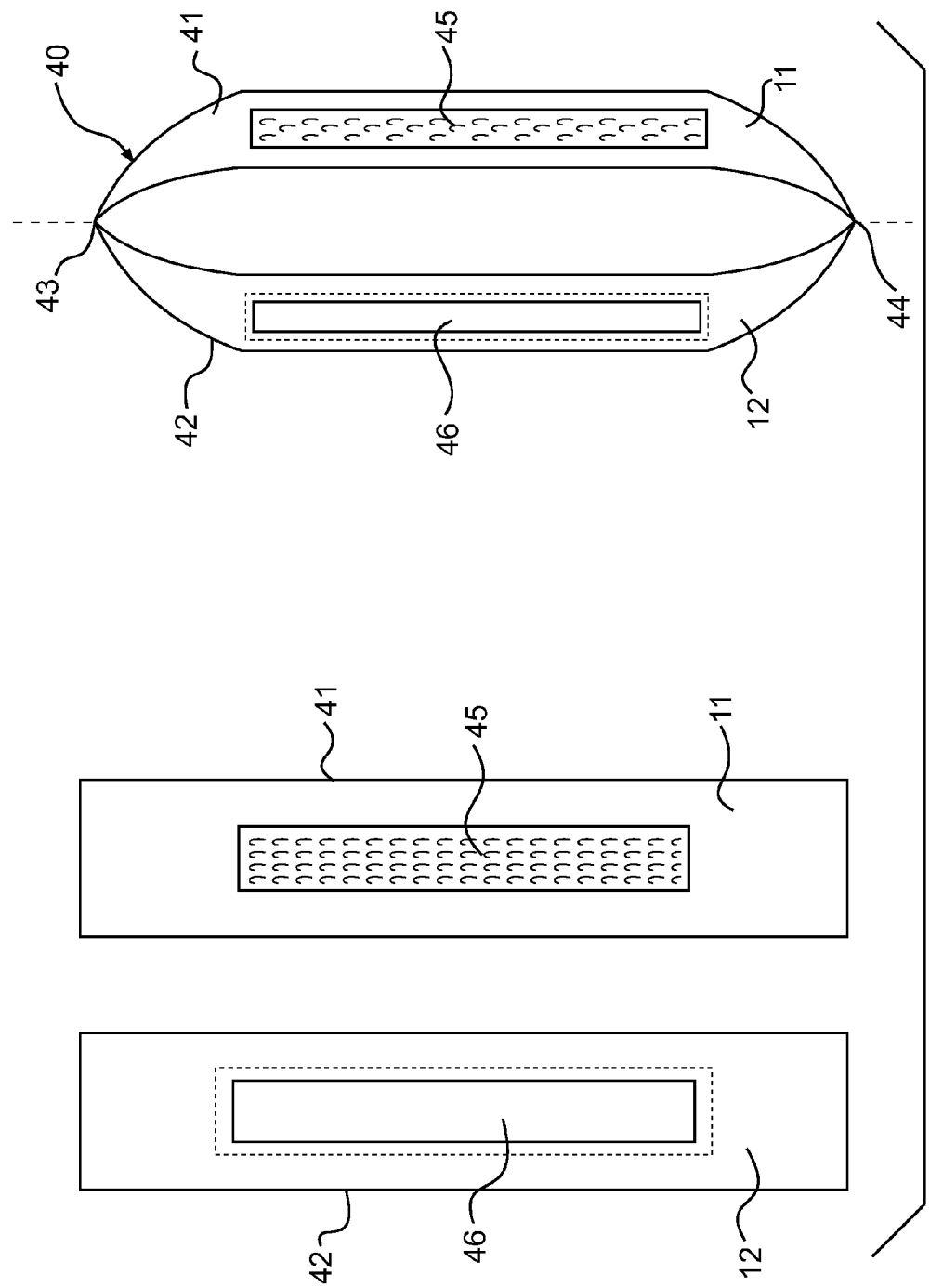
FIG. 6 is an enlarged fragmentary sectional view taken of the head opening.

The individual elements for forming the head opening 40 (also shown generally in FIG. 4, from the outside) are illustrated in FIG. 6. The head opening is illustratively formed from two rectangular sheets 41 and 42, which are made from layers 11, 12, and 13 and sewn together. The locking device to secure sheet 41 to sheet 42, when using the multipurpose sleeping bag 10 in the sleeping bag mode of operation, is formed by sewing a 1-inch-by-10-inch strip of hook-type fastener 45 to the center position of the external side 11 of rectangular sheet 41, and by sewing a 1-inch-by-10-inch strip of loop-type fastener 46 to the center position of the internal side 12 of rectangular sheet 42. In particular, Velcro may be used as the hook-and-loop fasteners. The rectangular sheets 41 and 42 are joined together at 43 and 44, and are then joined to multipurpose sleeping bag 10 by stitches around the radius of the head opening slit, forming a collar around the head opening 40. This gives the user the capability of closing the head opening 40 when using multipurpose sleeping bag 10 in the sleeping bag mode of operation. It is also an important feature that the edges of head opening 40 may be brought to fit about the wearer's neck when using the multipurpose sleeping bag 10 in the over garment modes of operation as shown in FIGS. 8, 9, and 10.

Figure 2:
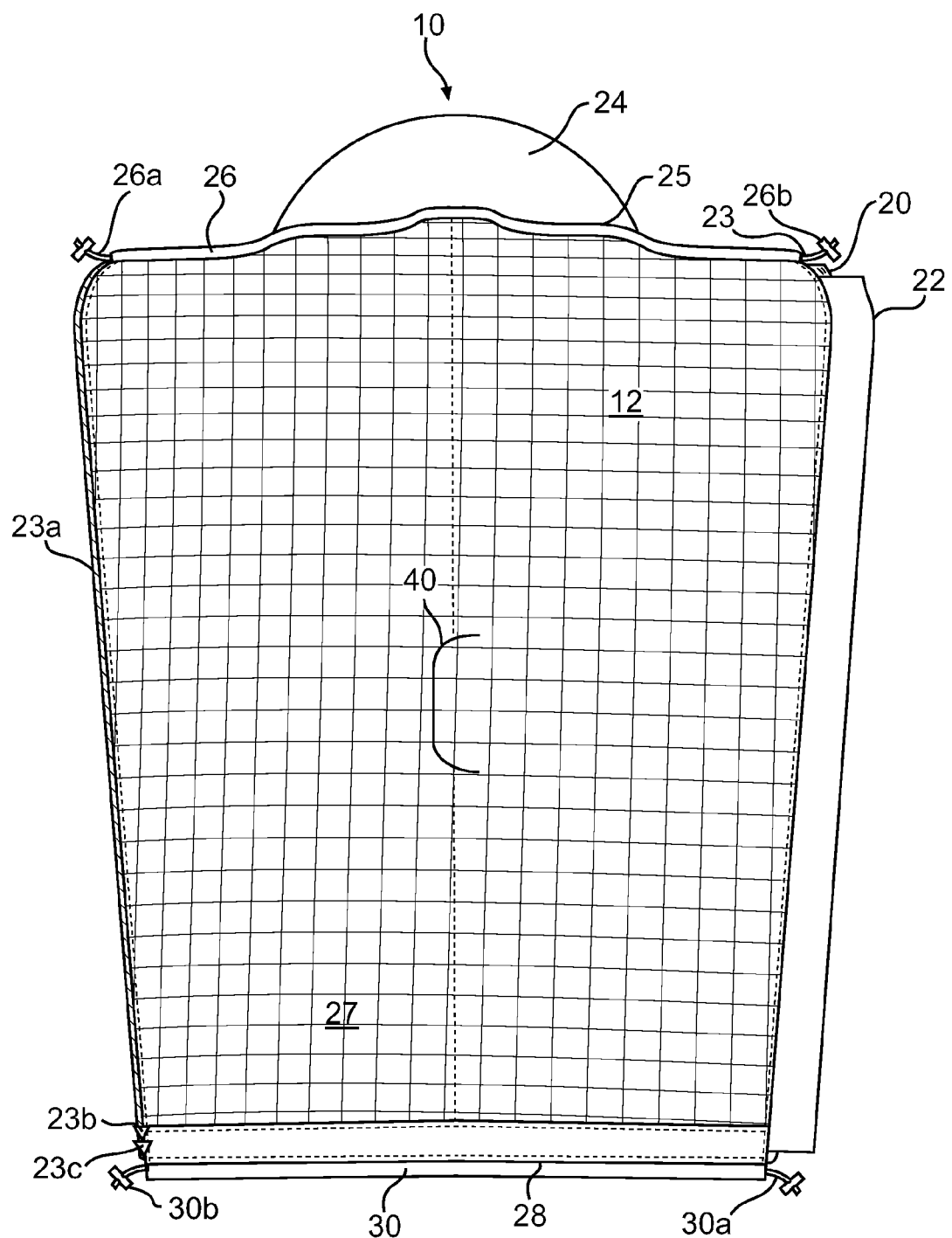
FIG. 2 is a perspective view with the head and foot ends open, exposing the inside of the multipurpose sleeping bag 10.
Figure 3:
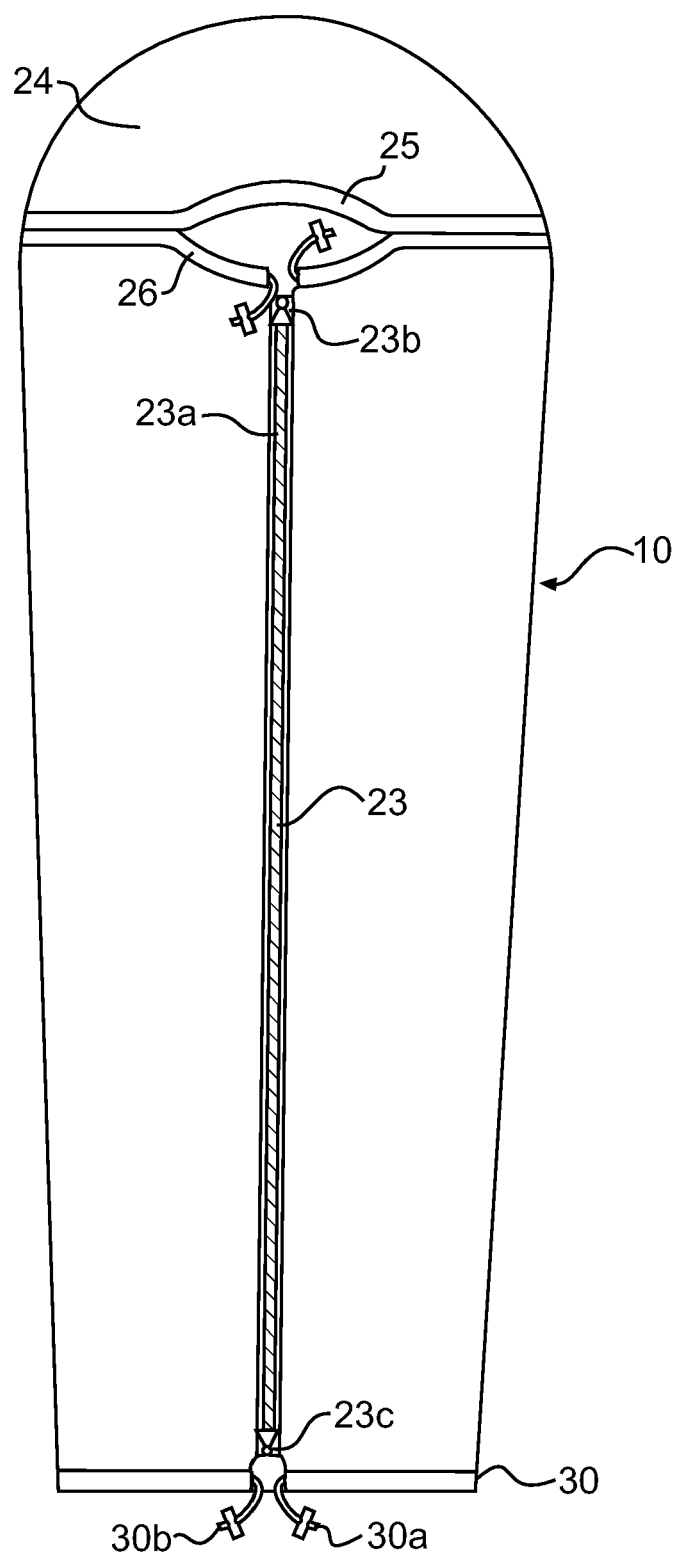
FIG. 3 is a perspective view of the front side (outside) of the multipurpose sleeping bag in the sleeping bag mode.
Figure 4:
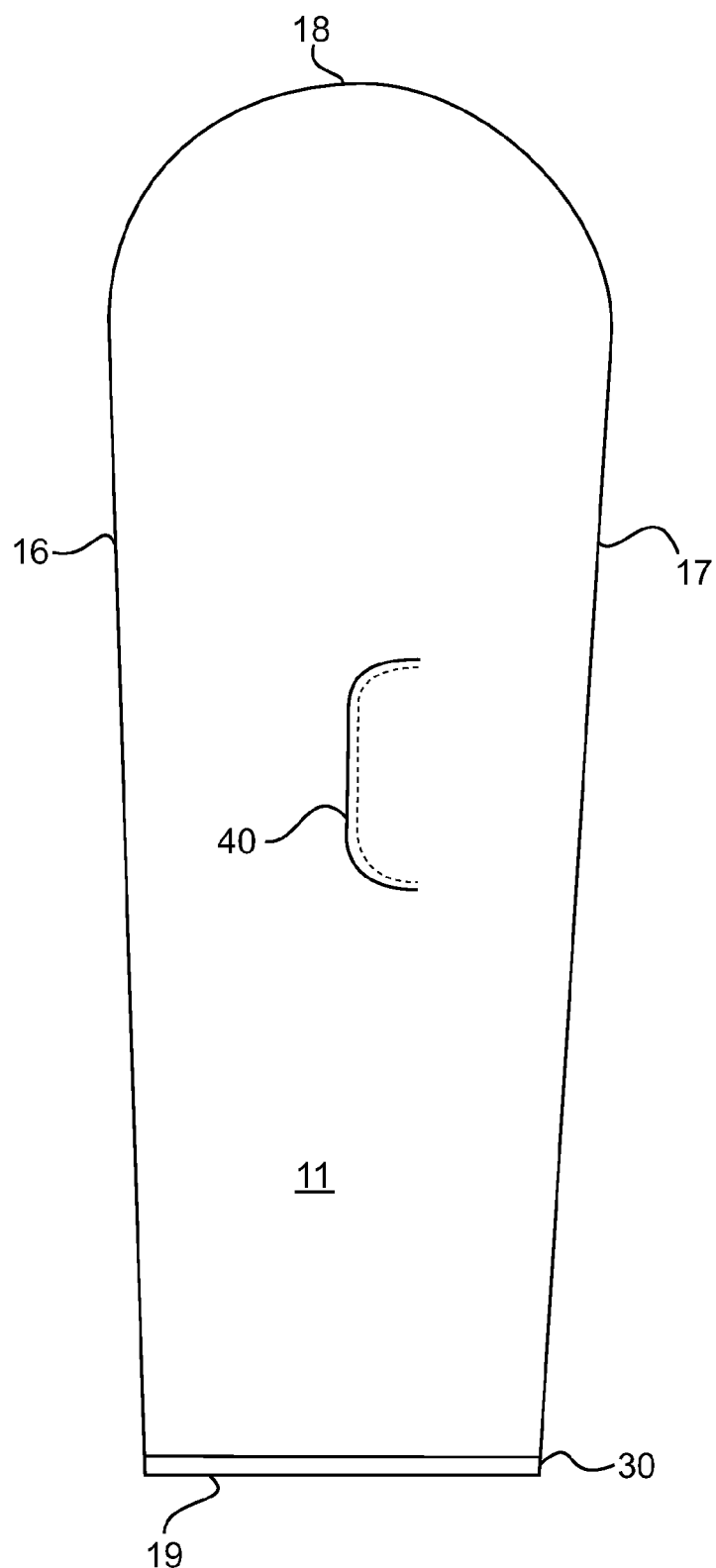
FIG. 4 is a perspective view of the back side (outside) of the multipurpose sleeping bag, showing the head opening.
Figure 5:
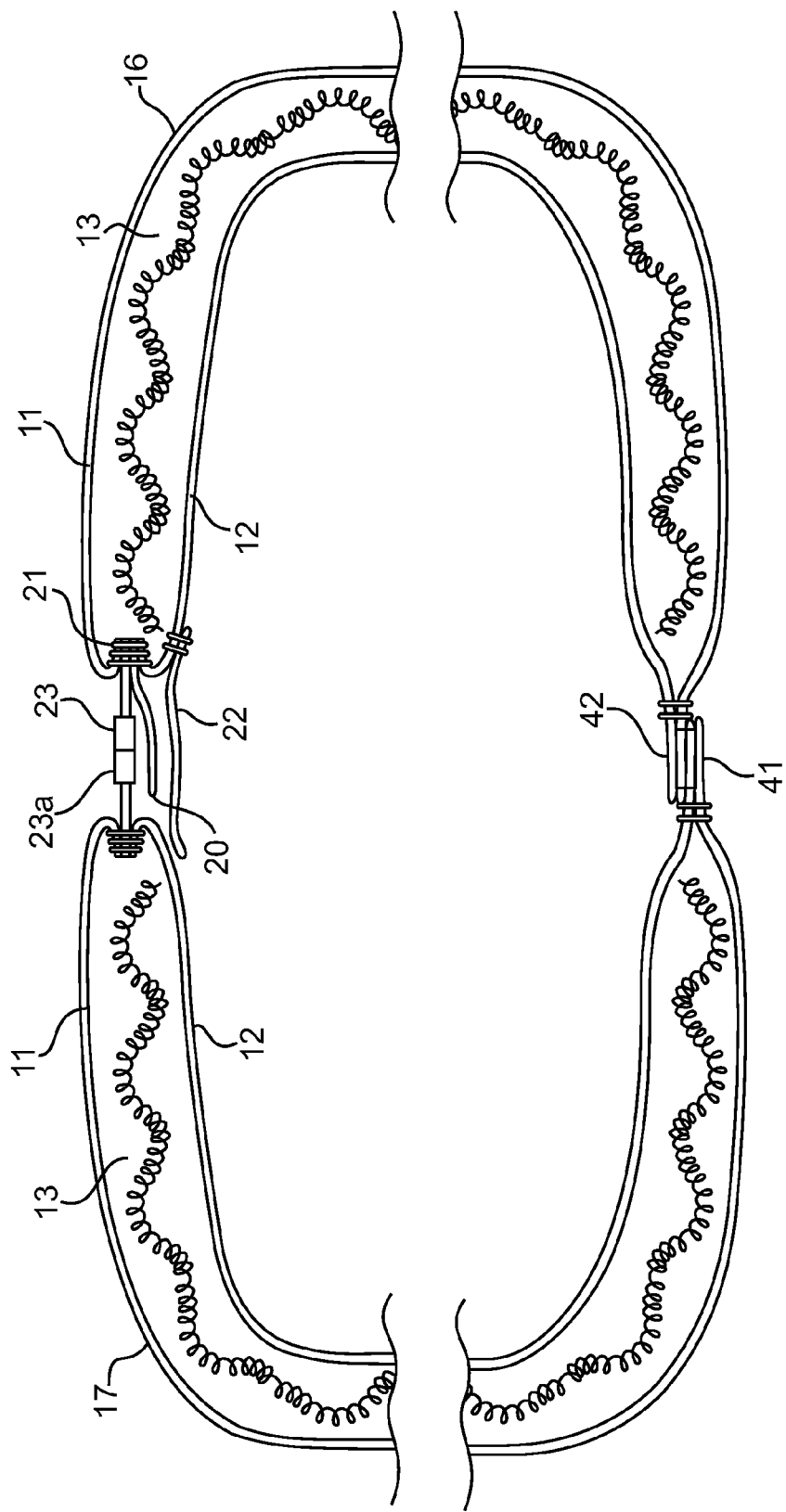
FIG. 5 is an enhanced fragmentary cross-sectional view illustrating the fastened zippers, the zipper guard and zipper draft tube attachments, the head opening, and the insulation material of a preferred embodiment.
Figure 8:
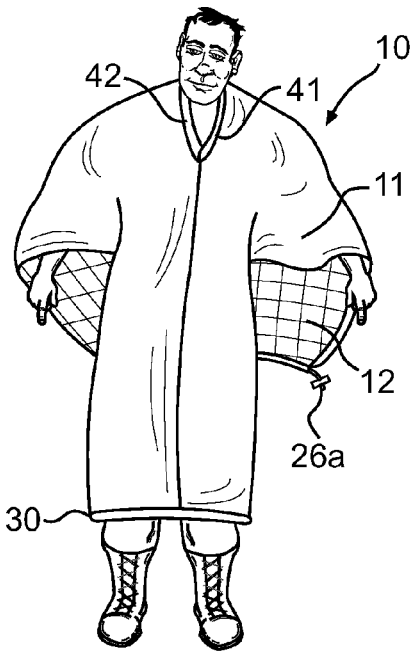
FIGS. 8-10 are perspective views illustrating the manner in which the multipurpose sleeping bag shown in FIG. 1 may be worn as a long coat, short coat, or poncho, respectively.

To form the cagoule or long coat as seen in FIG. 8, one begins with the multipurpose sleeping bag 10 as formed in FIG. 1. The foot draw cord 30a is unwrapped around the bottom "south" side 19 and spread out, as seen in FIG. 2. Then, zipper 23 is unzipped down to below the head opening 40, and sides 16 and 17 raised to approximately waist level. By stepping into the bottom "south" side 19 through the unzipped opening and holding the unzipped portion of the multipurpose sleeping bag 10 in front with zippers 23 and 23a facing the wearer (i.e., with the zipped lower portion behind the wearer), rectangular sheets 41 and 42 are grasped and pulled apart, permitting the wearer to insert his head into the head opening 40 from the inside, with rectangular sheets 41, 42 forming a collar. Then, sides 16 and 17 can be tossed over the head to configure the long coat. If desired, hood draw cord 26a can be drawn from one end of hood draw cord sleeve 26 while holding the other end, and tied off into a belt at the waist. Further, excess fabric from layers 11, 12, and 13 can be pushed to the back of the waist for best fit and a neater appearance.

Figure 9:
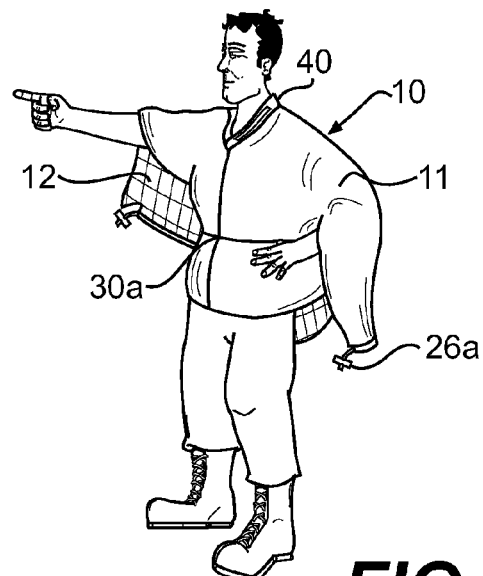

To form the anorak or short coat as seen in FIG. 9, from the long coat mode, the wearer reaches down and inside the multipurpose sleeping bag 10, grabs the ends of bottom or "south" portion 19, and raises up the ends approximately to waist level. By pulling the ends of foot draw cord 30a at the back of the waist, crossing them, and bringing them outside and around to the front of the waist, the ends of foot draw cord 30a can be tied off into a belt. Again, excess fabric of layers 11, 12, and 13 can be smoothed out to the back of the waist for best fit.

Figure 10:
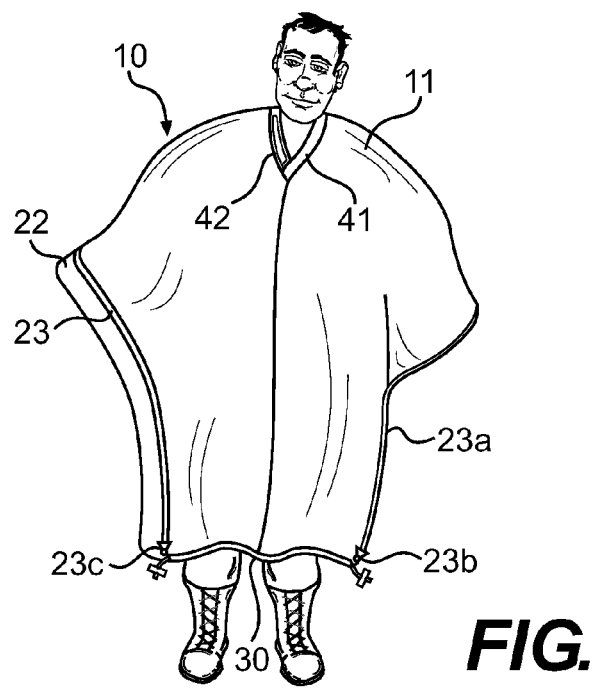

To form the poncho as seen in FIG. 10, the wearer begins with the multipurpose sleeping bag 10 as formed in FIG. 2. The zipper 23 is completely unzipped from zipper 23a of multipurpose sleeping bag 10 and laid flat with the outside fabric of layer 11 facing the ground. The multipurpose sleeping bag 10 is raised and the wearer puts his head through the head opening 40 and flips the hood end (top or "north" end) 18 over the shoulders.

A compressing stuff sack can be used to compress and carry multipurpose sleeping bag 10.

Figure 11:
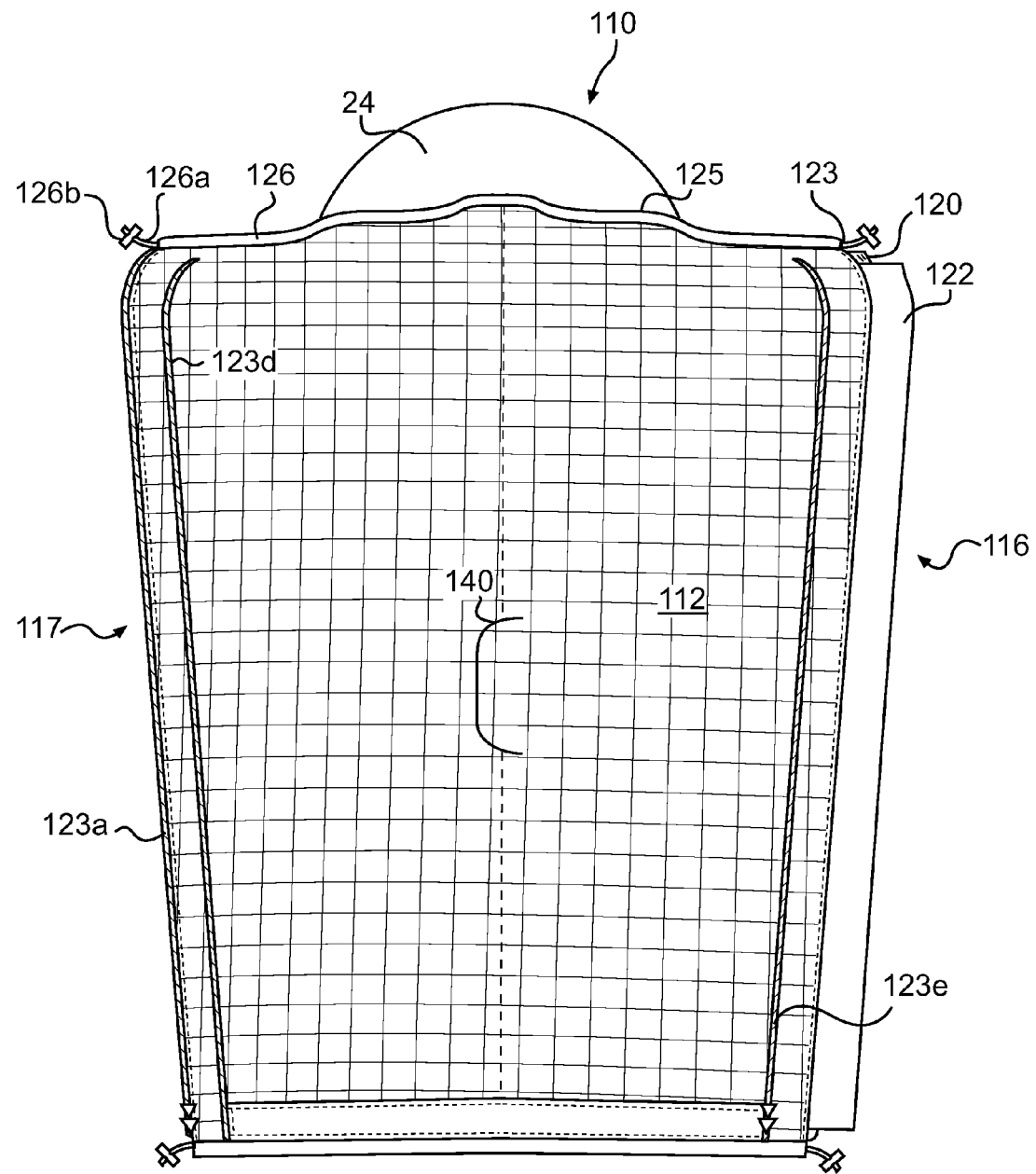
FIG. 11 is a perspective view with the head and foot ends open, exposing the inside and placement of the extra zipper 123e and 123d of the multipurpose over bag 110.

FIG. 11 shows an embodiment in which a second multipurpose sleeping bag is added as an over bag 110 to the multipurpose sleeping bag 10 described above, thereby creating a combination system 9 having increased thermal capacity. The over bag 110 has elements identical to those of bag 10, which are indicated by like reference numerals increased by 100, except that the over bag 110 has an extra zipper (123d and 123e) attached to it so as to be able to join the multipurpose sleeping bag 10 to the over bag 110.

However, the over bag 110 can provide even greater versatility for the wearer using insulation material of different weights. For example, the insulation material of over bag 110 (not shown, but similar to the insulation material 13) may be around 2.5 to 3 pounds for a temperature rating of +35° F. and up, while insulation material 13 of sleeping bag 10 may have an insulation filling of 4.5 pounds for a temperature rating of +20° F. Thus, when the weather is fairly mild and not expected to be below +35° F., the user who does not wish to carry the complete operational sleep system 9 simply unzips the over bag 110 from the multipurpose sleeping bag 10 and takes only over bag 110. If the temperature is to drop to between +35° F. and +20° F., only sleeping bag 10 is used, but if the temperature is to be colder than +20° F., multipurpose sleeping bag 10 is zipped to the over bag 110 and the system 9 of the two bags 10 and 110 protects down to about −25° F.

Referring to FIGS. 2 and 11, the combination system 9 is assembled by unzipping both bags 10 and 110 and laying them out by placing sleeping bag 10, as shown in FIG. 2, on top of the over bag 110, as shown in FIG. 11, so that the external shell 111 of over bag 110 is facing the ground, while the internal lining 112 is facing the external shell 11 of the multipurpose sleeping bag 10. Joining the bags is accomplished by zipping zipper 23 of the multipurpose sleeping bag 10 to zipper 123e of over bag 110 and by zipping zipper 23a of the multipurpose sleeping bag 10 to zipper 123d of over bag 110. To form the complete combination system 9, zipper 123 is simply zipped to zipper 123a of the over bag 110.

In another preferred embodiment of the present invention shown in FIGS. 12-21, it is possible to modify the multipurpose sleeping bag into a multipurpose hypothermia sleeping bag (MHSB). Indeed, in contrast with prior art efforts, this embodiment can provide modifications to any available mummy-type sleeping bag in providing controlled warmth to a person, including the embodiments disclosed above. In the following figures, elements corresponding to the above embodiments are designated by the same reference numerals, and description thereof is thus not repeated, for brevity.

Figure 12:
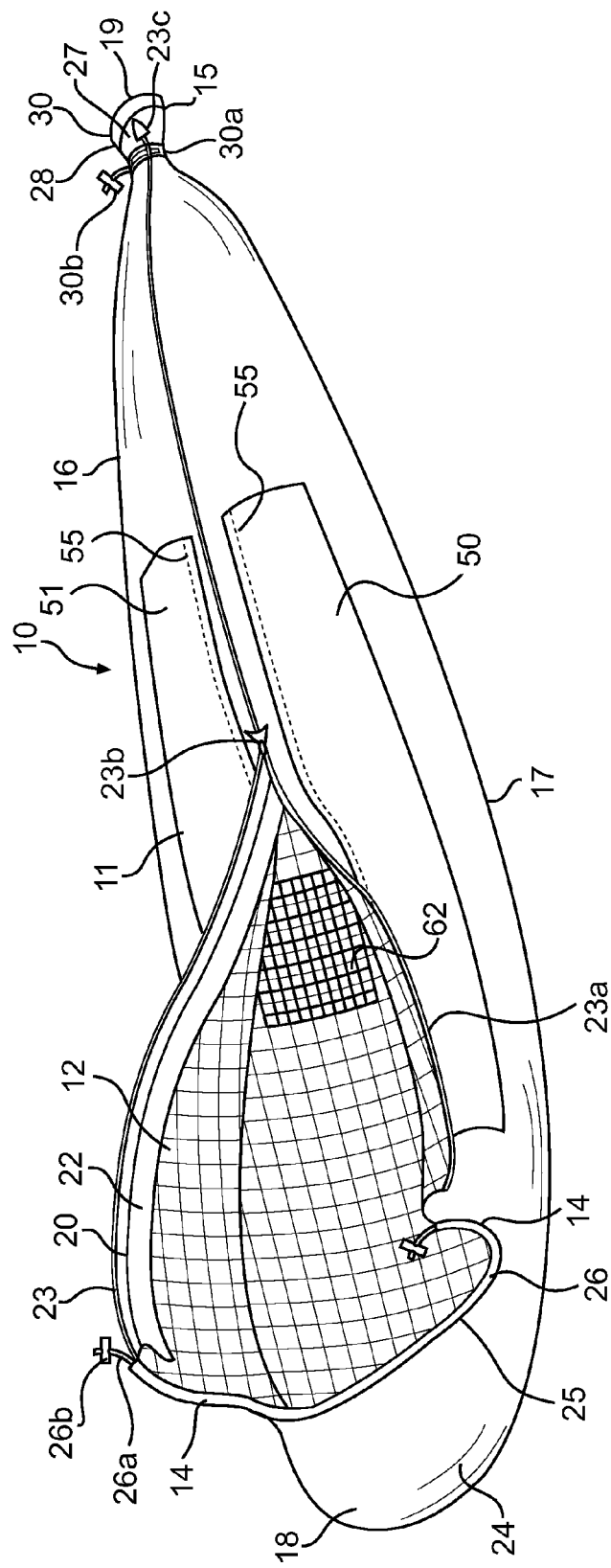
FIG. 12 is a perspective view illustrating a preferred embodiment of the invention as a multipurpose hypothermia sleeping bag.
Figure 13:
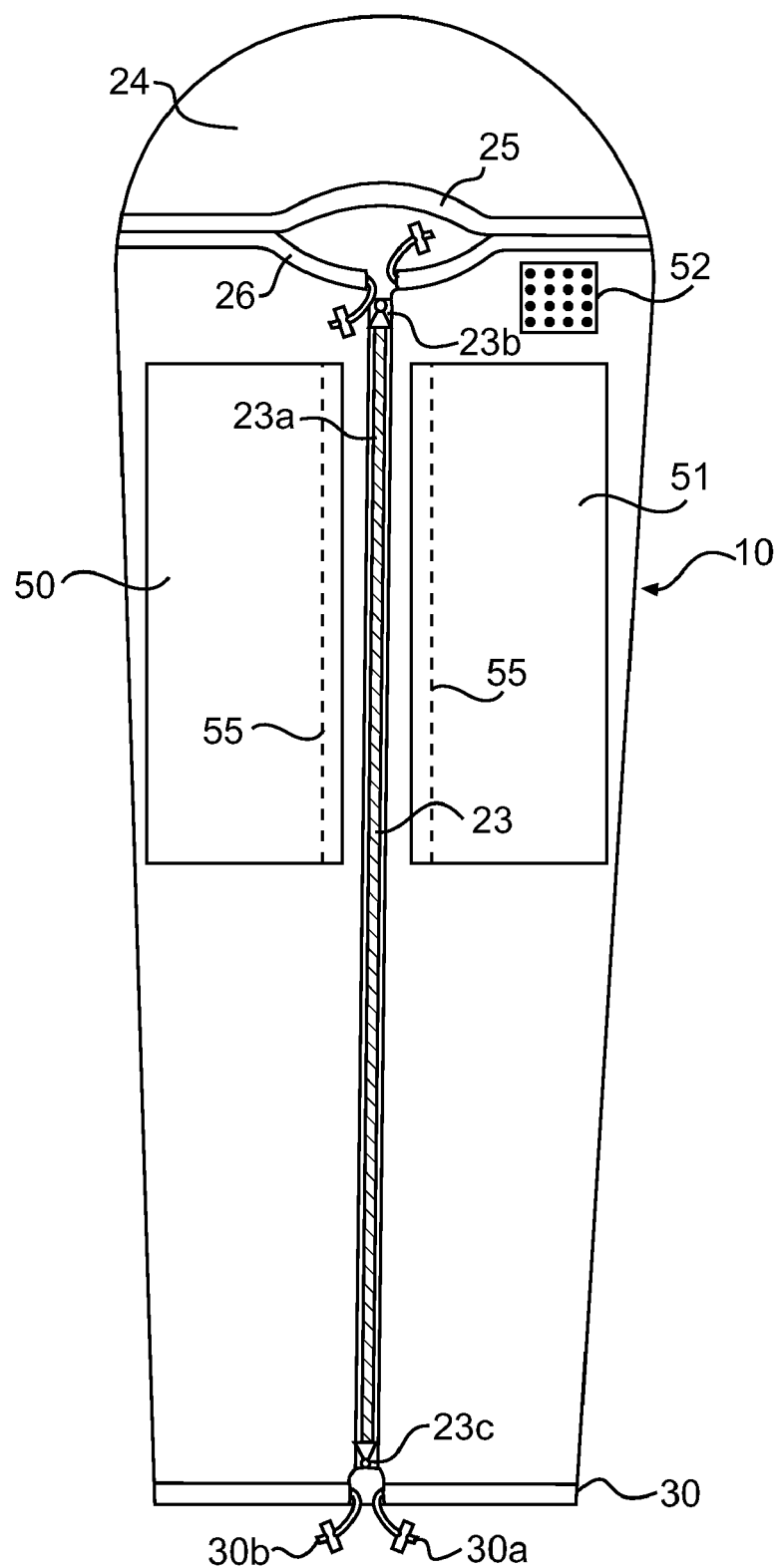
FIG. 13 is a perspective view of the front side (outside) of the multipurpose hypothermia sleeping bag zippered in the sleeping bag mode, showing the positioning of the torso and IV access panels in the sleeping bag mode.

In FIGS. 12 and 13, sleeping bag 10 can be viewed as comprising two front flaps (a left or "west" side flap 50 and a right or "east" side flap 51) for access to the patient's torso. Flaps 50, 51 may also be called the "upper torso and IV access flap panels", or simply "flap panels". As shown in FIG. 13, above flap 51 is a provision, such as a Velcro hook patch 52 to hold a heating control unit or the like to control heat to the sleeping bag 10 and its occupant.

Figure 14:
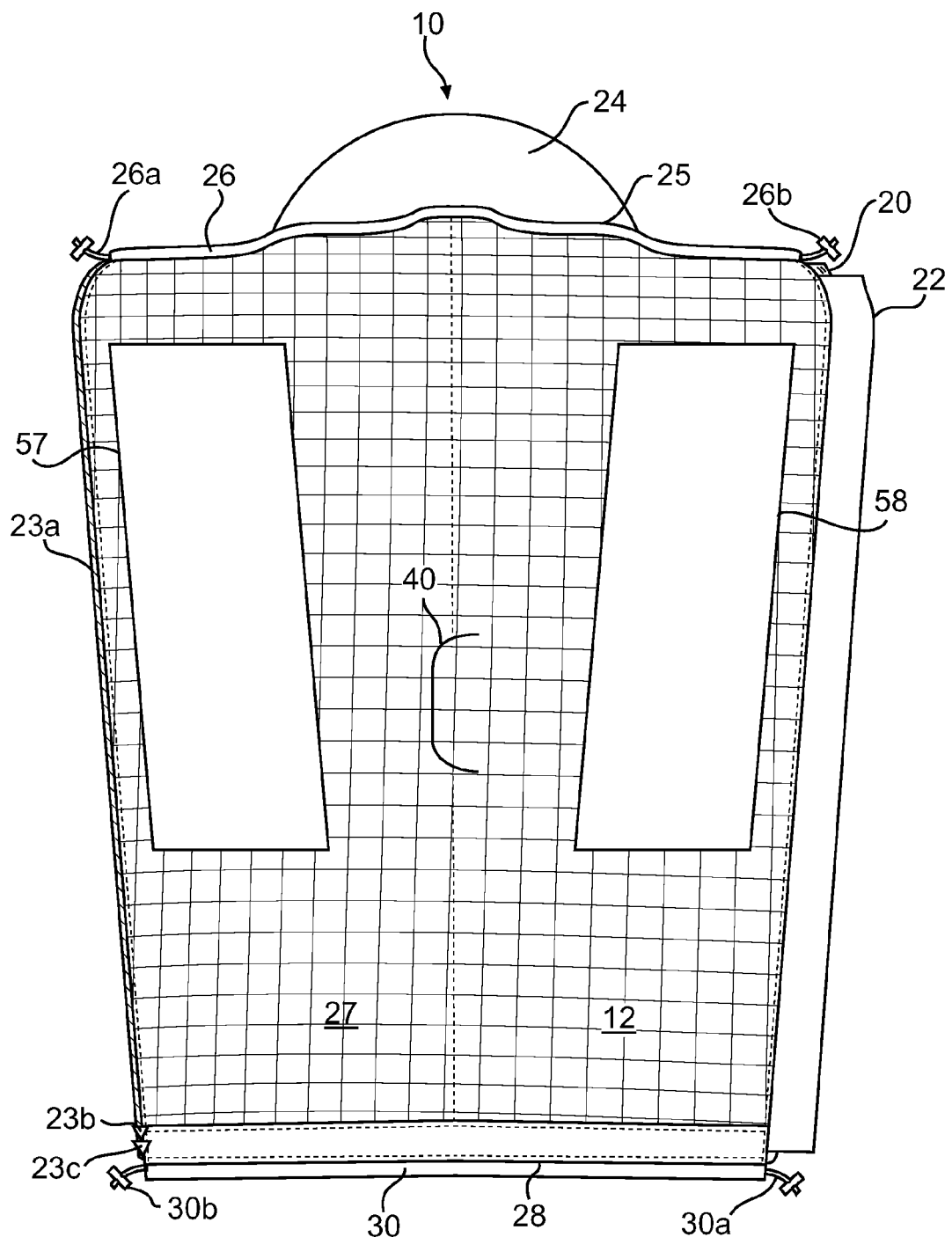
FIG. 14 is a perspective view of the multipurpose hypothermia sleeping bag, with the head and foot ends open, exposing the inside of the multipurpose hypothermia sleeping bag and cutouts for the right and left side torso and IV access panels, as well as the head opening.
Figure 15A:
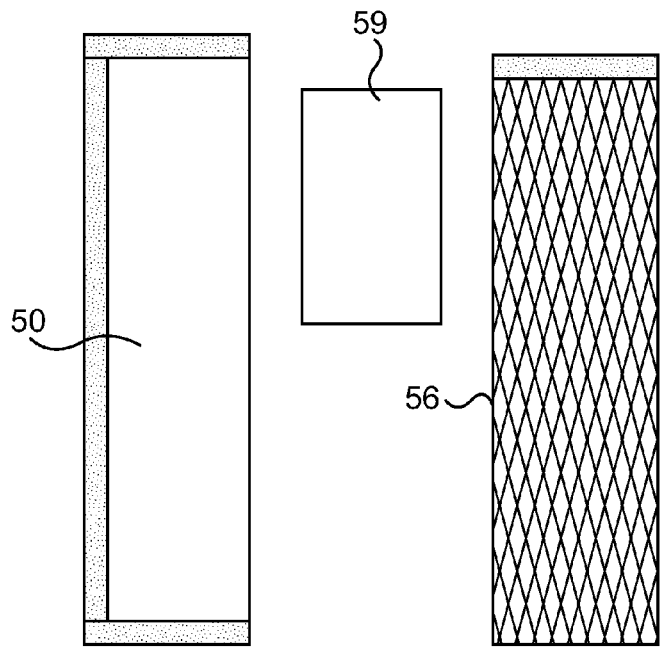
FIG. 15(*a*) is a partially broken front view of the sleeping bag of a torso and IV access flap and corresponding mesh panel, together with a heating unit normally inserted in a pocket formed by the torso and IV access panel and mesh panel.
Figure 15B:
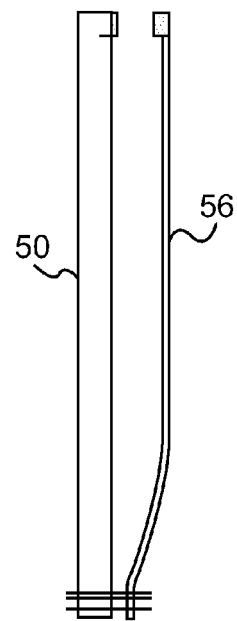
Figure 15C:
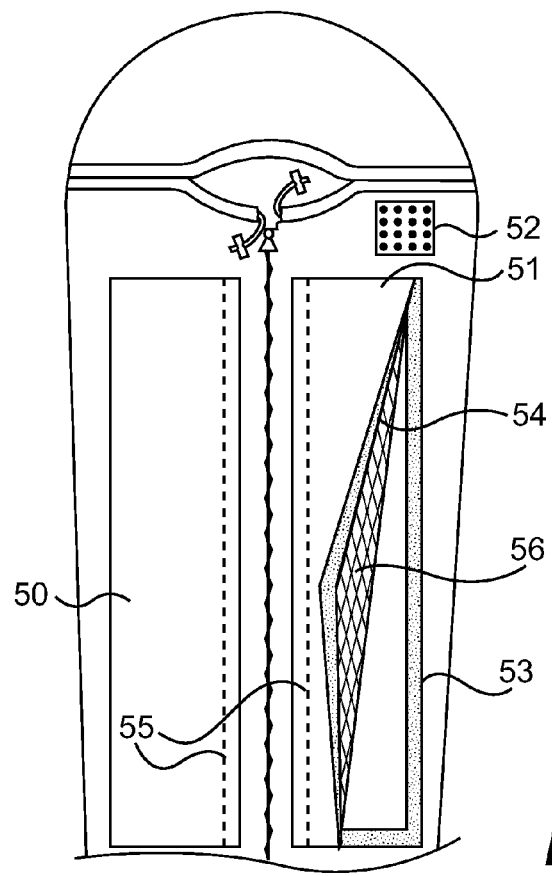

A fastener such as Velcro loops 53 is provided just outside the torso and IV access panel cutouts 58 and 57 (see, for example, FIG. 14), e.g., on three sides (north, east and south), corresponding to a fastener such as Velcro hooks 54 provided on three sides (north, east and south) of the flap panels 50, 51, so that the panels can be peeled back to provide open access to the occupant (e.g., FIG. 15(c)). A stitch line 55 is preferably positioned on the left (west side) of flap 51 and to the right (east side) of flap 50, as illustrated. Further, on the inside of either or both of the torso and IV access flap panels 50, 51 is attached (preferably sewn), to the north, east and south sides thereof, a mesh lining 56, designed thereby to form an access panel pocket which receives a heating unit for sleeping bag 10. This heating unit is placed between the mesh 56 and the flap panel 50 or 51 so as to provide warmth to a hypothermic patient or to provide warmth/heat to any IV lines coming into the bag 10. Similarly, a catheter can be routed in the same manner, as desired.

FIG. 14 shows, from the inside, the cutouts 57 and 58 for torso and IV access. The interior of the sleeping bag 10 also shows the head opening 40 for the user. This is brought to fit about the wearer's neck when using sleeping bag 10 in the over garment mode of operation, as described above.

In FIGS. 15(a)-15(c), the construction of the upper torso and IV access panel 50 shows the mesh lining 56 sewn to the external shell 11 as at 55, and to the upper torso and IV access flap panel 50. This is done in such a manner as to allow the insertion of the heating unit 59 in a pocket formed between the torso access panel 50 and the mesh 56. A similar arrangement may attach a mesh lining to flap panel 51. The side view (FIG. 15(b)) of the upper torso and IV access flap panel shows the top as the insertion point for the placement of the heating unit 59. If desired, the heating unit 59 can be kept in place by joining the hooks 54 and loops 53 on the three sides of the upper torso and IV access flap panels 50 and 51 and the corresponding torso and IV access panel cutouts 57 and 58. For example, a one-inch-wide Velcro hook site 54 is attached inside on the outer edge of the three sides, north, east and south of the upper torso and IV access flap panel 51, and a corresponding loop site 53 is attached on the outer edge of the three sides north, east and south of the torso and IV access panel cutout 57. Likewise, similar hook-and-loop sites are attached to the three sides, north, west and south of the upper torso and IV access flap panel 50 and corresponding panel cutout 58.

In addition to the foregoing description, a stitch line 55 is preferably placed to attach flap panels 50, 51 approximately ½ inch from the right side of panel cutout 57 and the left side of panel cutout 58, respectively, so that the upper torso and IV access flap panels 50 and 51 can be peeled away from sleeping bag 10 to have open access to a patient's torso.

Figure 16:
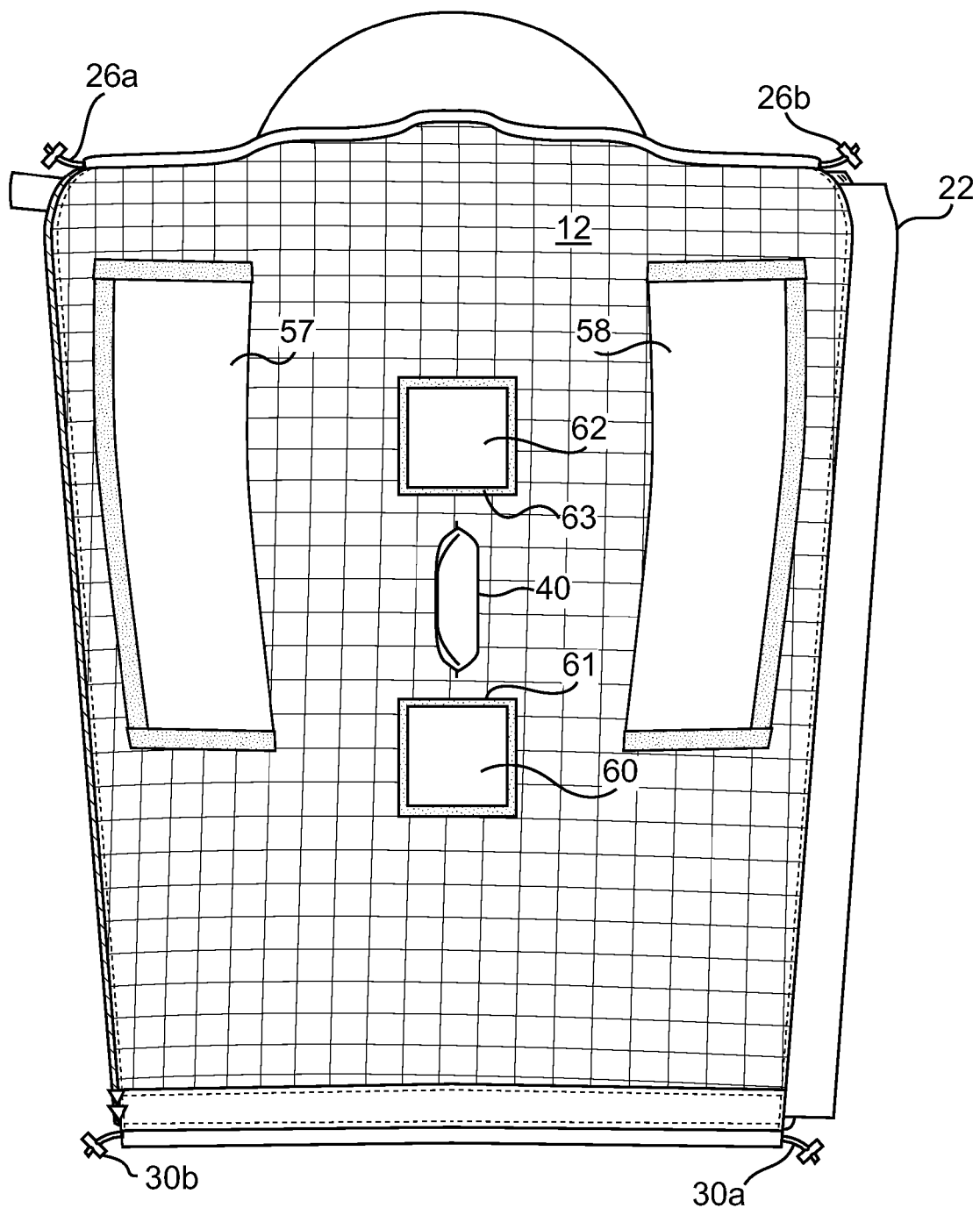
FIG. 16 is a perspective view with the head and foot ends of the multipurpose hypothermia sleeping bag open, illustrating the cutouts for torso and IV access and pockets for holding, e.g., heating units.

In the preferred embodiment, as best illustrated in FIG. 16, two pockets are additionally shown. The lower pocket, called the chest pocket 60, is directly below the head opening 40, and above the "south" side of sleeping bag 10, with the pocket opening 61 placed on the "north" side of chest pocket 60. In addition, the other pocket, called the back pocket 62, is directly above the head opening 40, and below the hood 24 of the sleeping bag 10, with its pocket opening 63 placed on the "south" side of the back pocket 62. The back pocket 62 is also shown illustratively in FIG. 12.

Figure 17:
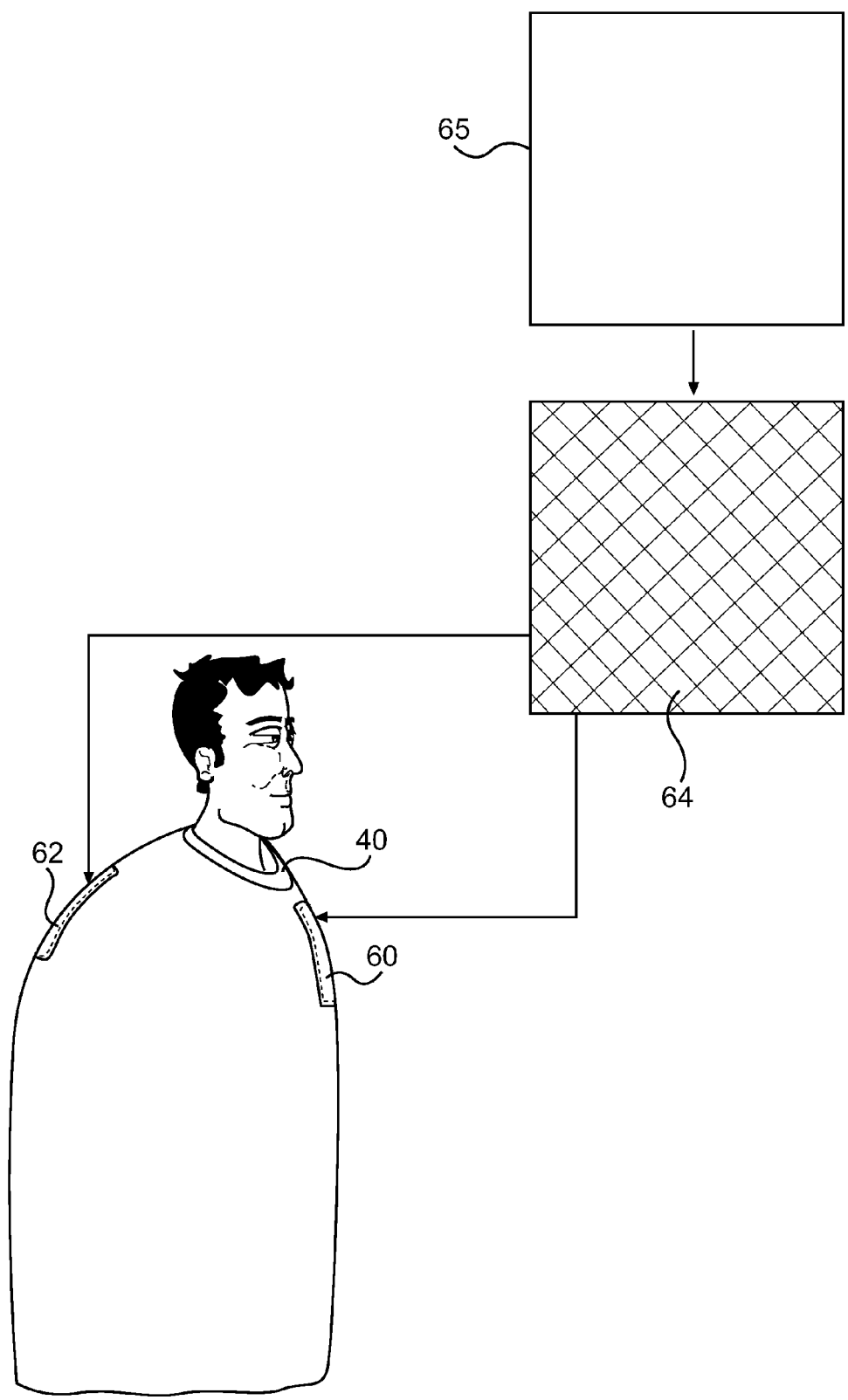
FIG. 17 is a perspective view illustrating the placement of the chest and back pockets.

As illustrated in FIGS. 16 and 17, the chest pocket 60 and back pocket 62 are preferably formed by sewing an 11" by 11" mesh 64, for example, to the inside of the sleeping bag 10 internal lining 12. A heating unit 65 can then be inserted from the top between the sleeping bag 10 and the mesh 64 in both pockets, so that the warmth of the wearer can be controlled while wearing the multipurpose sleeping bag 10 in one of the over garment modes of operation.

Figure 18:
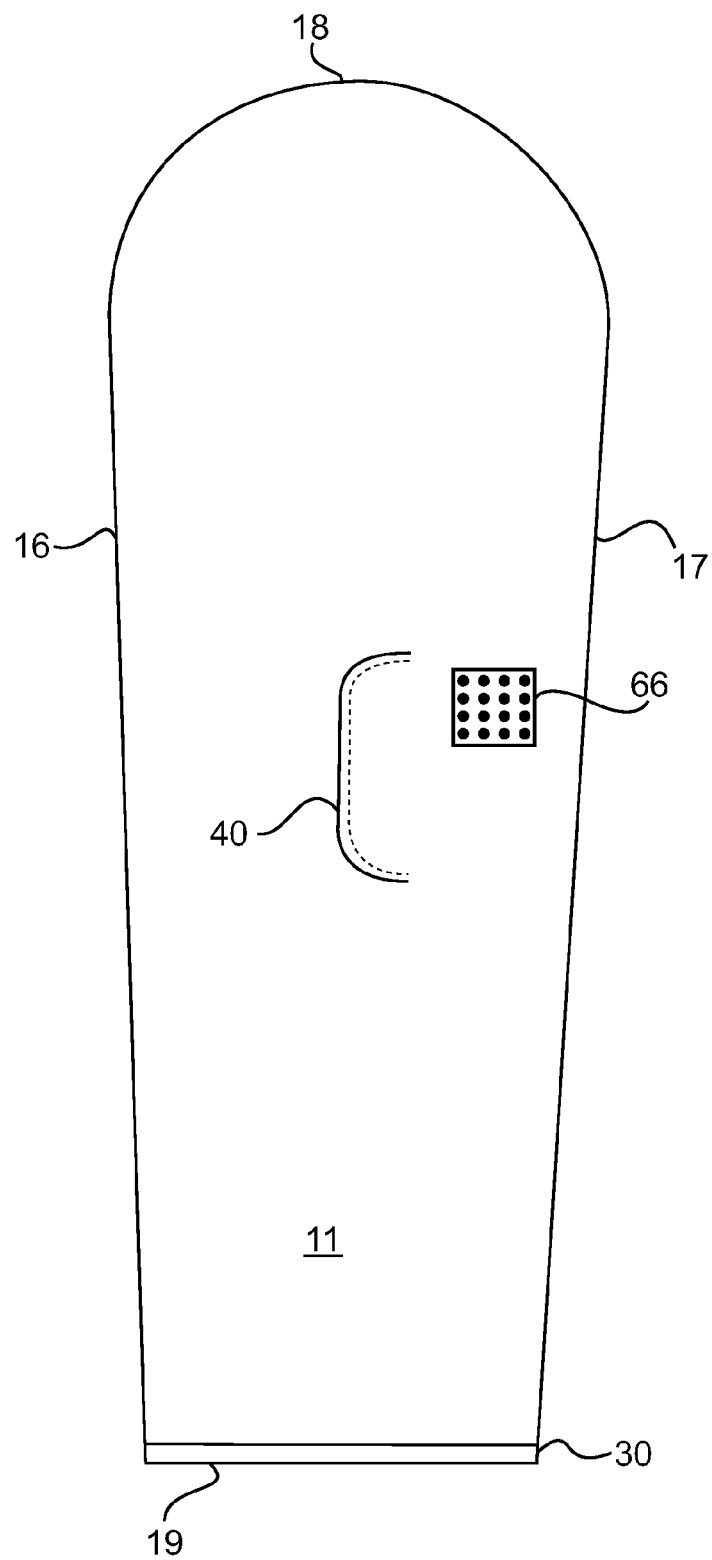
FIG. 18 is a perspective view of the back (outside) of the multipurpose hypothermia sleeping bag, showing a site for a warming device control unit.
Figure 19:
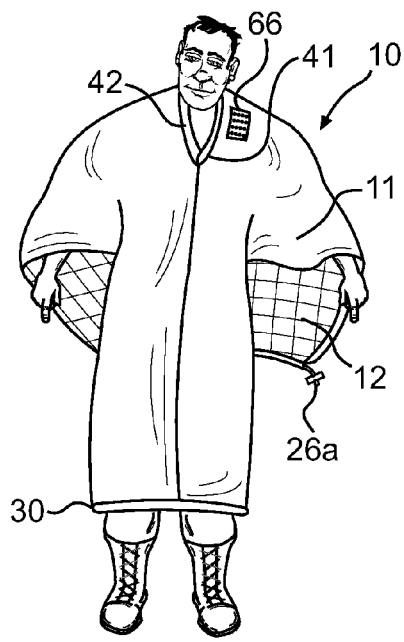
FIGS. 19-21 are perspective views illustrating the manner in which the multipurpose hypothermia sleeping bag shown in FIG. 12 may be worn as a long coat, poncho or short coat, respectively.
Figure 20:
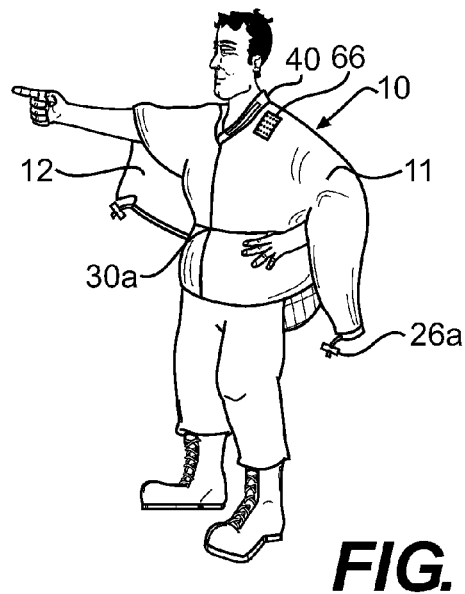
Figure 21:
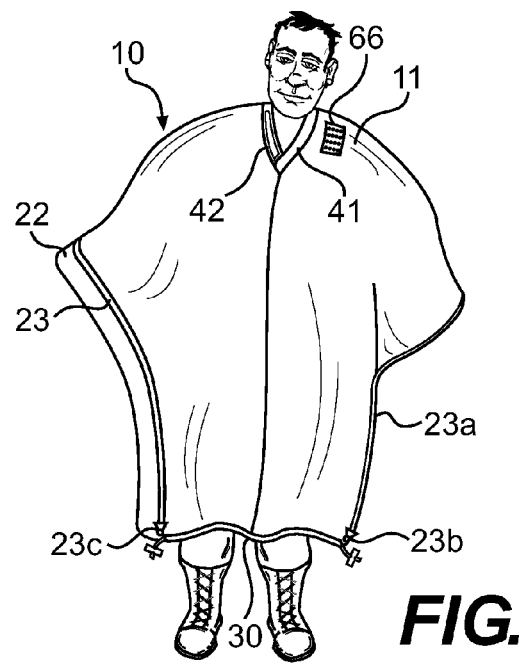

FIG. 18 shows a perspective view of the back side (outside) of the multipurpose hypothermia sleeping bag, showing a representative (e.g., 3"×3") site 66 (which may be Velcro sewn to the right side of the head opening 40), so that a control unit for the heating unit 65 can be provided. FIGS. 19-21 show the multipurpose hypothermia sleeping bag in the long coat, short coat, and poncho modes, respectively, each having the Velcro site 66.

In addition to the preferred embodiment described above, it is contemplated that any currently used sleeping bag structural material can be used effectively with the present invention. Outer shell materials, lining materials and filling materials that are presently employed can be used with this invention, as well as with sleeping bags, which are only a single or double thickness material. In addition, insulative pads can be inserted into any or all of the disclosed pockets as desired, to provide additional insulation for the wearer and/or the units contained therein. The provision of the closure elements, as described, can be accomplished with a minimal effect on the insulating properties desired in sleeping bags used for the outdoors.

From the foregoing, it can be seen that the foot end and the head opening of the present invention, by reason of both their shape and dimensional relationship to the individual user, provides a multipurpose capability for the user not heretofore present in a single sleeping bag. Further, the multipurpose sleeping bag can be modified as described above to provide a multipurpose hypothermia sleeping bag, including provisions for heating and heating control, as well as IV and torso access via flap panels provided for this purpose.

It is also to be understood that the foregoing disclosure describes only the preferred embodiments of the present invention, and that numerous alterations and modifications can be utilized to practice the present invention without departing from the scope and spirit of the invention as defined in the appended claims.

What is claimed is:

1. A multipurpose sleeping bag, comprising:
a body including first and second side edges each having a fastener adapted to fasten a length of each side edge to a length of the other side edge to configure the multipurpose sleeping bag in a sleeping bag mode of operation or in each of a plurality of over garment modes of operation, said fasteners extending from a foot portion of the body to a head portion thereof;
a head opening located substantially centrally in the body with respect to the first and second side edges thereof and with respect to the head and foot portions thereof, and substantially equidistant from the fasteners, the head opening being adapted to permit a wearer's head to project through the head opening such that the body rests on the wearer's shoulders in the over garment modes of operation;
first and second pockets located on opposite sides of the head opening, the first pocket being located between the head opening and the head portion of the body, and the second pocket being located between the head opening and the foot portion of the body, wherein in the over garment modes of operation, the first and second pockets are respectively located behind and in front of the wearer;
a first locking device adapted to selectively close the head opening to configure the multipurpose sleeping bag in the sleeping bag mode of operation, and to selectively open the head opening to configure the multipurpose sleeping bag in the over garment modes of operation;
a second locking device adapted to selectively close and open the foot portion such that the wearer is able to step into the multipurpose sleeping bag through the open foot portion with the first and second side edges fastened together by the fastener at the foot portion of the body, put the wearer's head through the head opening, and move an unfastened portion of the multipurpose sleeping bag over the shoulders to configure the multipurpose sleeping bag in at least one of the over garment modes of operation;
first and second flap panels located on opposite sides of the head opening, the first flap panel being located between the head opening and the first side edge of the body, and the second flap panel being located between the head opening and the second side edge of the body;
a first attachment device between the first flap panel and the head portion of the body;
first and second access panel cutouts in the body respectively located corresponding to the first and second flap panels, such that the first and second flap panels are arranged to cover said first and second access panel cutouts, respectively, and to selectively expose either of said first and second access panel cutouts for access to the wearer therethrough; and
a second attachment device located adjacent the head opening.

2. A multipurpose sleeping bag as claimed in claim 1, further comprising a hood element configured at the head portion of the body.

3. A multipurpose sleeping bag as claimed in claim 1, wherein when the first and second side edges are fastened together by the fasteners in the sleeping bag mode of operation, the head opening is located opposite to the fastened first and second side edges.

4. A multipurpose sleeping bag as claimed in claim 1, wherein the first locking device is a hook-and-loop fastener.

5. A multipurpose sleeping bag as claimed in claim 1, wherein the second locking device comprises a foot draw cord sleeve and a foot draw cord located in the foot draw cord sleeve, such that when the multipurpose sleeping bag is fastened in the sleeping bag mode of operation, the foot draw cord is wrapped around the foot portion to thereby close off the foot portion.

6. A multipurpose sleeping bag as claimed in claim 1, further comprising a mesh panel arranged between one of the first and second access panel cutouts and the corresponding first or second flap panel, said mesh panel being attached to the flap panel so as to constitute a receiving cavity for receiving an article.

7. A multipurpose sleeping bag as claimed in claim 6, further comprising a heating unit in said receiving cavity.

8. A multipurpose sleeping bag as claimed in claim 6, further comprising at least one IV line routed through said receiving cavity.

9. A multipurpose sleeping bag as claimed in claim 6, further comprising at least one insulative pad in said receiving cavity.

10. A multipurpose sleeping bag as claimed in claim 1, further comprising a heating unit attached to said first attachment device.

11. A multipurpose sleeping bag as claimed in claim 10, further comprising a control unit for controlling the heating unit, wherein the control unit is attached to said second attachment device.

12. A multipurpose sleeping bag as claimed in claim 1, wherein the multipurpose sleeping bag further comprises a heating unit in at least one of said first and second pockets.

13. A multipurpose sleeping bag, comprising:
a body including first and second side edges each having a fastener adapted to fasten a length of each side edge to a length of the other side edge to configure the multipurpose sleeping bag in a sleeping bag mode of operation or in each of a plurality of over garment modes of operation, said fasteners extending from a foot portion of the body to a head portion thereof;
a head opening located substantially centrally in the body with respect to the first and second side edges thereof and with respect to the head and foot portions thereof, and substantially equidistant from the fasteners, the head opening being adapted to permit a wearer's head to project through the head opening such that the body rests on the wearer's shoulders in the over garment modes of operation;
a first locking device adapted to selectively close the head opening to configure the multipurpose sleeping bag in the sleeping bag mode of operation, and to selectively open the head opening to configure the multipurpose sleeping bag in the over garment modes of operation;
a second locking device adapted to selectively close and open the foot portion such that the wearer is able to step into the multipurpose sleeping bag through the open foot portion with the first and second side edges fastened together by the fastener at the foot portion of the body, put the wearer's head through the head opening, and move an unfastened portion of the multipurpose sleeping bag over the shoulders to configure the multipurpose sleeping bag in at least one of the over garment modes of operation;
first and second flap panels located on opposite sides of the head opening, the first flap panel being located between the head opening and the first side edge of the body, and the second flap panel being located between the head opening and the second side edge of the body;
first and second access panel cutouts in the body respectively located corresponding to the first and second flap panels, such that the first and second flap panels are arranged to cover said first and second access panel cutouts, respectively, and to selectively expose either of said first and second access panel cutouts for access to the wearer therethrough; and
a mesh panel arranged between one of the first and second access panel cutouts and the corresponding first or second flap panel, said mesh panel being attached to the flap panel so as to constitute a receiving cavity for receiving an article.

14. A multipurpose sleeping bag as claimed in claim 13, further comprising a heating unit in said receiving cavity.

15. A multipurpose sleeping bag, comprising:
a body including first and second side edges each having a fastener adapted to fasten a length of each side edge to a length of the other side edge to configure the multipurpose sleeping bag in a sleeping bag mode of operation or in each of a plurality of over garment modes of operation, said fasteners extending from a foot portion of the body to a head portion thereof;
a head opening located substantially centrally in the body with respect to the first and second side edges thereof and with respect to the head and foot portions thereof, and substantially equidistant from the fasteners, the head opening being adapted to permit a wearer's head to project through the head opening such that the body rests on the wearer's shoulders in the over garment modes of operation;
first and second pockets located on opposite sides of the head opening, the first pocket being located between the head opening and the head portion of the body, and the second pocket being located between the head opening and the foot portion of the body;
a heating unit selectively disposed in at least one of said first and second pockets;
a first locking device adapted to selectively close the head opening to configure the multipurpose sleeping bag in the sleeping bag mode of operation, and to selectively open the head opening to configure the multipurpose sleeping bag in the over garment modes of operation whereby the first and second pockets are respectively located behind and in front of the wearer;
a second locking device adapted to selectively close and open the foot portion such that the wearer is able to step into the multipurpose sleeping bag through the open foot portion with the first and second side edges fastened together by the fastener at the foot portion of the body, put the wearer's head through the head opening, and move an unfastened portion of the multipurpose sleeping bag over the shoulders to configure the multipurpose sleeping bag in at least one of the over garment modes of operation, whereby the first and second pockets are respectively located behind and in front of the wearer;
first and second flap panels located on opposite sides of the head opening, the first flap panel being located between the head opening and the first side edge of the body, and the second flap panel being located between the head opening and the second side edge of the body; and
first and second access panel cutouts in the body respectively located corresponding to the first and second flap panels, such that the first and second flap panels are arranged to cover said first and second access panel cutouts, respectively, and to selectively expose either of said first and second access panel cutouts for access to the wearer therethrough.

16. A multipurpose sleeping bag as claimed in claim 15, further comprising a mesh panel arranged between one of the first and second access panel cutouts and the corresponding first or second flap panel, said mesh panel being attached to the flap panel so as to constitute a receiving cavity for receiving an article.

17. A multipurpose sleeping bag as claimed in claim 16, further comprising a heating unit in said receiving cavity.

* * * * *